United States Patent [19]
Margerum et al.

[11] Patent Number: 6,010,681
[45] Date of Patent: *Jan. 4, 2000

[54] BIODEGRADABLE BLOOD-POOL CONTRAST AGENTS

[75] Inventors: Larry Margerum, Wayne, Pa.; Brian Campion, Solano Beach, Calif.; Jere Douglas Fellmann, Livermore, Calif.; Martha Garrity, San Clemente, Calif.; John Varadarajan, Sunnyvale, Calif.

[73] Assignee: Nycomed Salutar, Inc., Wayne, Pa.

[*] Notice: This patent issued on a continued prosecution application filed under 37 CFR 1.53(d), and is subject to the twenty year patent term provisions of 35 U.S.C. 154(a)(2).

[21] Appl. No.: 08/722,080

[22] PCT Filed: Apr. 20, 1995

[86] PCT No.: PCT/GB95/00899

§ 371 Date: Jan. 21, 1997

§ 102(e) Date: Jan. 21, 1997

[87] PCT Pub. No.: WO95/28967

PCT Pub. Date: Nov. 2, 1995

[30] Foreign Application Priority Data

Apr. 20, 1994 [GB] United Kingdom .................. 9407812
Oct. 13, 1994 [GB] United Kingdom .................. 9420657

[51] Int. Cl.[7] .................................................. A61B 5/055
[52] U.S. Cl. .................... 424/9.35; 424/9.36; 424/9.364; 424/9.42
[58] Field of Search .............................. 424/9.36, 9.364, 424/9.35, 9.42; 600/420; 436/173

[56] References Cited

FOREIGN PATENT DOCUMENTS

90/12050 10/1990 WIPO .
93/06868 4/1993 WIPO .

OTHER PUBLICATIONS

Tilcock et al., "Nuclear magnetic relaxation dispersion and phosphorus–32 NMR studies of the effect of covalent modification of membrane surfaces with poly(ethylene glycol)", *Biochim. Biophys. Acta*, 1110(2): 193–8, 1992, (Abstract only).

Torchilin et al, "Targeted Delivery of Diagnostic Agents by Surface Modified Liposomes" *Journal of Controlled Release*, 28:45–58, 1994.

Torchilin et al., "Polymers on the Surface of Nanocarriers: Modulation of Carrier Properties and Biodistribution" *Vysokomol. Soedin., Ser. A. Ser. B*, 36(11):1880–1893, 1994, (Abstract only).

Trubetskoy et al., "Controlled Delivery of Imaging Agents to Lymph Notes: Membranotropic Polychelating Agent for Incorporation into Liposomes" *Proc. Int. Symp, Controlled Release Bioact. Mater.*, 20:380–381, 1993, (Abstract).

Wiener et al., "Dendrimer–Based Metal Chelates: A New Class of MRI Contrast Agents" *Magnetic Resonance in Medicine*, 30(1):1–8, 1994.

Primary Examiner—Gary E. Hollinden
Attorney, Agent, or Firm—Fish & Richardson P.C.

[57] ABSTRACT

The invention provides a blood pool contrast agent having an overall molecular weight of at least 10KD comprising a macrostructure which has bound thereto a plurality of opsonization inhibiting moieties and carries chelated ionic paramagnetic or heavy metal moieties, the chelant groups for said chelated moieties being macrocyclic where said macrostructure is liposomal.

15 Claims, No Drawings

BIODEGRADABLE BLOOD-POOL CONTRAST AGENTS

This invention relates to diagnostic imaging contrast agents and in particular to blood pool agents, that is contrast agents which have a long residence time in the vasculature.

Medical imaging modalities, such as MR imaging, X-ray, PET, SPECT, magnetotomography, EIT, gamma-scintigraphy and CT scanning are becoming extremely important tools in the diagnosis and treatment of illnesses. Some imaging techniques can rely entirely on the inherent attributes of body components, such as bone and soft tissue, to achieve differentiation in the images between such components, others require the administration of agents (contrast agents) to permit such differentiation or to improve the image contrast between different such components or between viable and damaged tissue.

The use of contrast agents is well established in most imaging modalities.

The efficacy of a contrast agent, however, is dependant not only on its inherent capacity to improve image contrast in the imaging modality in question but also upon its pharmacokinetics, ie. its spatial and temporal distribution pattern following administration.

For contrast agents administered into the systemic vasculature, as a general rule, low molecular weight hydrophilic molecules (e.g. molecular weight beneath 5000 D) distribute into the extracellular fluid (ECF) and are relatively rapidly excreted through the kidneys by glomerular filtration, whereas particulates, liposomes or lipophilic molecules tend to accumulate relatively rapidly in the liver.

Several ECF and liver contrast agents are marketed or are in clinical development. However, while various blood pool agents (i.e. agents which do not distribute into the ECF and yet have relatively prolonged residence times in the blood pool) have been proposed, their development has not yet progressed very far.

Thus, in the field of MR imaging, early suggestions for blood pool agents included paramagnetic chelate-macromolecule conjugates, e.g. where the macromolecule was a soluble biotolerable material such as dextran with a molecular weight above the kidney threshold and where the chelate was for example GdDTPA. Later suggestions involved the proposal that polychelants, high molecular weight water soluble species capable of chelating many, e.g. 20–100, paramagnetic metal ions be used.

The materials proposed have encountered problems of poor characterization, unpredictable biodistribution, unsatisfactory blood pool residence times, liver accumulation, and inadequate bioelimination by glomerular filtration.

The demand for effective and tolerable blood pool agents, therefore still exists.

We now propose a novel class of blood pool contrast agents which have opsonization controlling moieties bound to a macrostructure which carries chelated paramagnetic or heavy metal ions.

Viewed from one aspect, therefore, the invention provides a blood pool contrast agent having an overall molecular weight of at least 10 KD (preferably at least 15 KD and especially about 20 KD or greater) comprising a macrostructure which has bound thereto a plurality of opsonization inhibiting moieties and carries chelated ionic paramagnetic or heavy metal moieties, the chelant groups for said chelated moieties being macrocyclic where said macrostructure is liposomal.

Opsonization is the process by which blood proteins attach to foreign matter in the vasculature to facilitate the rapid uptake of such matter by the reticuloendothelial system (RES), primarily liver, spleen and bone marrow.

Various opsonization inhibitors may be used according to the invention but in general they will be amphiphilic polymers, optionally terminally modified, e.g. for attachment to the macrostructure. By an amphiphilic polymer is meant a polymer having repeat units with lipophilic and hydrophilic segments. A preferred example of such a polymer is polyethyleneglycol which has a [CH$_2$CH$_2$O] repeat unit, the alkylene chain providing the lipophilic segment and the ether oxygen providing the hydrophilic segment.

Thus the opsonization inhibitor moieties used according to the invention are conveniently of formula I

$$-A-(R_1R_2)_n-B \qquad (I)$$

where A is a bond or a functional group allowing attachment to the macrostructure, e.g. the residue of a group with a labile hydrogen or other displaceable atom or group, for example the residue of a carboxyl, hydroxy, amine, succinyl, nitrophenylcarbamate or thiol group or of a phosphorus, sulphur or boron oxyacid, linked to $(R_1R_2)_n$ by a bond or a linker moiety, e.g a $C_{1-8}$ alkylene chain; one of $R_1$ and $R_2$ is a lipophilic moiety, e.g. a $C_{1-8}$ alkylene chain optionally unsaturated and optionally substituted or interrupted by an aryl or cycloalkyl group, e.g. phenyl or cyclohexyl, and the other of $R_1$ and $R_2$ is a hydrophilic moiety, e.g. an oxa, thia or aza group or a $C_{1-8}$ alkylene chain interrupted or substituted by groups selected from oxa, aza, thia, amine, thiol, hydroxy, oxo, thio, imido, sulphinyl, sulphonyl and phosphono; n is an integer having a value of from 3 to 200, especially 5 to 100, more especially 10 to 80; and B is a terminal group, e.g. a hydrogen atom or a hydrophilic or hydrophobic group, or a paramagnetic or heavy metal chelate moiety.

It will be appreciated from the above that the chelated paramagnetic or heavy metal moiety in the diagnostic agent of the invention may be bound to the macrostructure directly or via an intermediary group, and that while such intermediary groups may function simply as linkers they may also function as opsonization inhibitors.

Especially preferred as opsonization inhibitors are moieties containing as the repeat unit $R_1R_2$, alkyleneoxy, alkylenethio and alkyleneimino groups and in particular such groups wherein the alkylene moiety is ethylene or propylene. Most particularly preferred are polyethyleneglycol (PEG) based opsonization inhibitors.

Methods for the attachment of PEG and PEG-derivatives are reviewed for example in Crit. Rev. in Therapeutic Drug Design 9: 249 (1992) and Rev. Macromol. Chem. Phys. C25: 325 (1985).

The chain length of the inhibitor affects its ability to inhibit opsonization and with PEG-like inhibitors the optimum molecular weight seems likely to be in the range 1 to 10 KD.

As an alternative to the amphiphilic polymers such as PEG, glycosaminoglycan moieties may alternatively be used as the opsonization inhibitors. In this respect, particular mention may be made of heparin, heparan, dermatan, keratan and chondroitin, and especially chondroitin-4-sulphate. These may, of course, be derivatised for attachment to the macrostructure, or where applicable to chelate structures. Generally, the glycosaminoglycans used will be about 10 to 100, especially 20 to 60, disaccharide units in length. Such materials are commercially available, e.g. from Sigma.

Other polymers such as polyols, polyvinylpyrrolidone, polyvinylalcohol, and further inhibitors as described in GB9407812.8 (a copy of which is filed herewith) and derivatives thereof may be used as the opsonization inhibitors. What is in general required for this function to be performed by a polymer is: water solubility; low interaction with the macrostructure, e.g. with the core of an aggregate macrostructure; low toxicity; low interaction with plasma proteins; and the ability to form a "brush" or "looped" structure extending outwardly from the macrostructure which deters protein binding.

The macrostructure in the contrast agents of the invention may be of unitary construction, e.g. a particulate, a polychelant or a dendrimeric polymer, or alternatively it may comprise a plurality of individual components held together by physicochemical effects, e.g. a liposome or a molecular aggregate.

The ultimate bioelimination route for at least the metal chelate moieties in the contrast agents of the invention is preferably renal, and thus where the macrostructure is eventually to be abstracted by the RES it is preferred that chelate attachment should be via biodegradable bonds which on cleavage release fragments which are renally excretable, e.g. with a molecular weight of less than 20 KD, preferably less than 10 KD, especially 200 to 5000 D. This is especially important where the macrostructure is particulate or liposomal.

The macrostructure in the contrast agents of the invention will generally take one of four forms: a particulate; a liposome; a molecular aggregate; or a high molecular weight molecule (e.g. a polychelant such as described in WO-90/12050).

Of these, the latter three are preferred and the latter two are especially preferred due to their greater liability to facilitate renal excretion than RES uptake of the chelate moieties.

Molecular aggregates are particularly interesting in this regard as they allow the possibilities of extended blood pool residence as well as renal excretion (by aggregate erosion causing the gradual loss of aggregate components which are below the kidney filtration threshold). In general, such structures can be generated using amphiphilic molecular components of formula II

C—D—E  (II)

where C is a hydrophilic, metal chelate containing moiety, D is an opsonization inhibiting linker and E is a hydrophobic moiety.

In formula II, as in the other materials according to the invention, the metal chelating moiety preferably comprises a macrocyclic chelant, e.g. as described in WO-93/06868. Other chelant moieties can, of course, also be used and many such moieties have been described in the scientific and patent literature in relation in particular to MR contrast agents. The reader is referred particularly to the published patent applications of Schering, Nycomed Salutar, Nycomed Imaging, Bracco, Mallinckrodt, Guerbet and Squibb. Macrocyclic and acyclic chelant moieties as described in GB9407812.8 are especially preferred.

The opsonization inhibiting linker in the aggregate component is preferably a material such as described above, e.g. a polyalkylene glycol, especially PEG, or a glycosaminoglycan. The hydrophobic moiety preferably comprises an alkyl or aryl group or a steroid, vitamin, porphyrin or phthalocyanin.

One particularly preferred molecular aggregate is based on phthalocyanine with conjugated thereto opsonization inhibitor groups and optionally, for example via such inhibitor groups, paramagnetic or heavy metal chelate groups. The phthalocyanine moiety here can act both as a hydrophobic moiety and as a metal chelating moiety.

Other amphiphilic molecules, however, may be used to form such aggregates and will generally have the formula

C—D—E or

C—E—D—B where $C^1$ is a metal chelate group attached to a hydrophobic group E directly or via a linker moiety and C, B, D and E are as described above. $C^1$ may be hydrophilic or hydrophobic and may be a conventional chelating moeity as discussed above for C in formula II. Of these two structures, the former which places the chelate moieties to the periphery of the aggregate is the preferred structure for $T_1$ MR contrast agents.

Generally the inhibitor will constitute 15–85% especially 30–80% of the weight of the aggregate component and the overall molecular weight of the individual molecular components of the molecular aggregates according to the invention is desirably less than 15 KD, especially 200 to 10000 D particularly 500 to 5000 D. The use of aggregates of this nature ensures that aggregate erosion in the vasculature results in the loss of fragments which are readily excreted renally even though the aggregate as a whole has a prolonged retention time in the blood pool. Renal excretion, the most rapid bioelimination route for most conventional ECF agents, is of course preferred as problems of toxicity associated with heavy metal retention in the body are minimized.

In the case of liposomal contrast agents according to the invention, the metal chelate may be free within the liposome central cavity or alternatively it may be carried by the liposome membrane, and in the latter case it may be disposed on the interior or exterior membrane of the liposome. For $T_1$ MR contrast agents, it is preferred that the chelate be disposed on the exterior of the liposome to maximize interaction of the paramagnetic centres with the surrounding body fluid. For the liposomal contrast agents however, it may be preferred that the chelate be on the liposome's exterior and linked to the liposome by a biodegradable bond.

By carrying the chelate on the liposome surface it is also possible to use particularly small liposomes, e.g. 50–100 nm diameter, and thereby delay RES uptake.

For the liposomal macrostructures, the opsonization inhibitors should, of course, be linked to the liposome's exterior.

The preparation of liposomal contrast agents is already a well established technique and conventional methods and conventional liposome membrane forming materials may be used in the production of the contrast agents of the invention. Thus, for example, amphiphilic liposome membrane forming materials, such as lipids and in particular phospholipids may be used to form the basic liposomal structure which acts as the carrier for chelate and opsonization-inhibiting moieties.

Liposomal agents will generally include, besides the chelate carrying molecules and the liposome membrane forming compounds, the materials which make up the liposome core and its external environment, generally in each case an aqueous medium.

The liposomes themselves are spherical vesicles having a lipid bilayer surrounding a central space. The present invention is particularly concerned with unilammellar and multilamellar liposomes which respectively have a single lipid bilayer or multiple lipid bilayers surrounding an aqueous core.

Liposomes spontaneously form upon dispersion of lipids, particularly phospholipids, in aqueous media and the liposomal structure of the agents of the invention can be produced by conventional techniques. Such conventional techniques are referred to in WO 92/21017 (Unger) and by Papahadjopolous in Ann. Rep. Med. Chem. 14: 250–260 (1979) and include reverse evaporation, freeze-thaw, detergent dialysis, homogenization, sonication, microemulsification and spontaneous formation upon hydration of a dry lipid film. Multi-lamellar liposomes can be used according to the invention or may be converted to liposomes with lower lamellarity, or to unilamellar liposomes, by known methods. Unilamellar liposomes can also be prepared directly.

Liposome preparations are typically heterogeneous in size and the liposomes used according to the invention may be sized to the desired diameter by known techniques, eg. extrusion, freeze-thaw, mechanical fragmentation, homogenization and sonication. The liposomes used according to the invention are advantageously 20–400 nm diameter, unilamellar or multi-lamellar.

The liposomes may be lyophilized to increase shelf life and lyophilized liposomes may be reconstituted by vigorous shaking with aqueous buffer prior to use. Formulations may include agents which serve to stabilize the liposomal material for the lyophilization procedure.

Liposomes smaller than 200 nm may be sterilized after formulation by filtration through a 0.2 μm filter to remove pyrogens.

The lipids used as the liposomal membrane forming molecules are typically phospholipids such as natural or synthetic phosphatidylcholines (lecithins) (PC), phosphatidylethanolamines (PE), lysolecithins, lysophosphatidylethanolamines, phosphatidylserines (PS), phosphatidylglycerols (PG), phosphatidylinositol (PI), sphingomyelins, cardiolipin, phosphatidic acids (PA), fatty acids, gangliosides, glucolipids, glycolipids, mono-, di or triglycerides, ceramides or cerebrosides, eg. liposome membrane forming compounds such as are described in WO-92/21017.

The membrane forming lipids may also comprise polymerizable lipids, eg. methacrylate lipids, thiol and disulphide lipids, dienoate lipids, styryl lipids and diacetylanic lipids as described by Johnston in Liposome Technology Vol. I, Gregoriades Ed., pages 123–129 (1983) and Singh in Phospholipid Handbook, Cevc Ed., Dekker, pages 233–291 (1993) and references therein. The use of polymerizable lipids in the formation of the liposomes provides one route for increasing liposome stability.

The liposomal membrane can also have steroids and other compounds incorporated into it, eg. to affect the biodistribution of the liposome. Suitable steroids include for example cholesterol, cholesterol derivatives, cholestane, cholic acid, and bile acids, but particularly cholesterol.

The inclusion of steroids serves to modify the fluidity of the liposome membrane and this affects biodistribution. Thus higher transition temperature lipids lead to longer blood half lives and the inclusion of cholesterol results in a more rigid and less permeable bilayer. A decrease in RES-uptake is observed with the addition of cholesterol.

The opsonization inhibitors can be incorporated by the use of a phospholipid derivative having a pendant opsonization inhibiting function, by the use of an inhibtor agent having a hydrophobic "anchor" moiety which associates with the liposomal membrane or by coupling an opsonization inhibiting agent to an "anchor" molecule present in the liposomal membrane, e.g. a lipid liposome membrane forming molecule.

Particularly preferred opsonization inhibitors include compounds, especially amphiphilic polymers, which serve to reduce in vivo protein binding to the liposome and thus prolong the half life of the liposomes in the blood. Polyalkyleneoxy polymers, such as polethylene glycol (PEG) and gangliosides, such as $Gm_1$, are effective in this regard.

Incorporation of 1–10%, relative to the weight of liposome membrane forming material, of PEG-PE derivatives significantly extends blood half life.

Liposomes prepared from perfluorinated phospholipids (see Santaella, FEBS Letters 336: 481–484 (1993) and Angew. Chem. Int. Ed. Eng. 30: 567–568 (1991)) can also extend blood half-lives.

Active targetting to specific organs or tissues can be achieved by incorporation of lipids with attached thereto monoclonal antibodies or antibody fragments that are specific for tumor associated antigens, lectins or peptides.

Liposome biodistribution is also significantly dependent upon surface charge and the liposomes according to the invention may desirably include 1 to 10%, relative to the weight of liposome membrane forming material, of negatively charged phospholipids such as for example phosphatidylserine, phosphatidylglycerols, phosphatidic acids, and phosphatidylinositol.

The chelated metals can be tethered to the liposomes in several ways, for example:

(i) by metallation of chelant groups tethered to the surface of preformed liposomes;

(ii) by coupling chelate moieties to anchor molecules in preformed liposomes;

(iii) by forming liposomes using a lipid mixture including chelate:anchor molecules.

All three methods represent aspects of the present invention but the second is the most preferred. This process simplifies the procedure for preparing membrane bound agents by avoiding the synthesis and purification of hydrophobic chelates (implicit in process (iii)) and by avoiding the unwanted weak (easily reversible in vivo) binding of metal to liposome that is associated with process (i).

The liposomes of the invention preferably are produced by coupling metallated chelate molecules to anchor molecules in pre-prepared liposomes. In this way the chelate is only bound to the exterior of the liposome membrane. Liposomes which are formed with derivatized chelates have the complex attached to both the interior and exterior of the membrane. The water permeability of the membrane or rate of diffusion of the bulk water through the membrane will determine the relaxivity of the inner paramagnetic ions. With tight, stable liposomes, the relaxivity of gadolinium inside the liposome may be very low. Thus with the chelate groups tethered only to the liposome exterior the efficiency of usage of the metal is optimized, ie. the liposomes have a high relaxivity per metal ion.

Having the chelates linked only to the exterior of the liposomes is also an advantage for binding radionuclides, especially α-emitters, since the membrane of the liposome does not have to be penetrated by the alpha rays.

Thus the liposomes may be prepared by a conventional method from a phospholipid mixture which includes the anchor compound, a compound having a hydrophobic anchor moiety tethered to a reactive functional group which provides an attachment point for the chelate moiety. The liposomes can then be sized to the required diameter by known methods. The reactive functional group is then coupled to a compatible functional group on the chelate and the unreacted low molecular weight chelate can readily be removed, eg. by gel permeation chromatography, dialysis or ultrafiltration.

The anchor compound conveniently comprises 10–80% relative to the total weight of the liposome membrane forming compounds, preferably 10–50%, especially 25–50%. The coupling efficiency, of the chelate to the externally directed reactive groups that is, can be very high indeed, eg. about 90%.

The reactive groups on the anchor compound may simply be primary amines on a liposome membrane lipid which can be reacted with a non-coordinating carboxyl group of a chelate molecule. In general most known methods of coupling chelates to macromolecules, such as proteins, may be used for chelate attachment to liposomes. The surface chemistry will however be limited by liposome stability and thus monitoring the pH and osmolality of the reaction mixture may be desirable. A few examples of coupling strategies are illustrated schematically below:

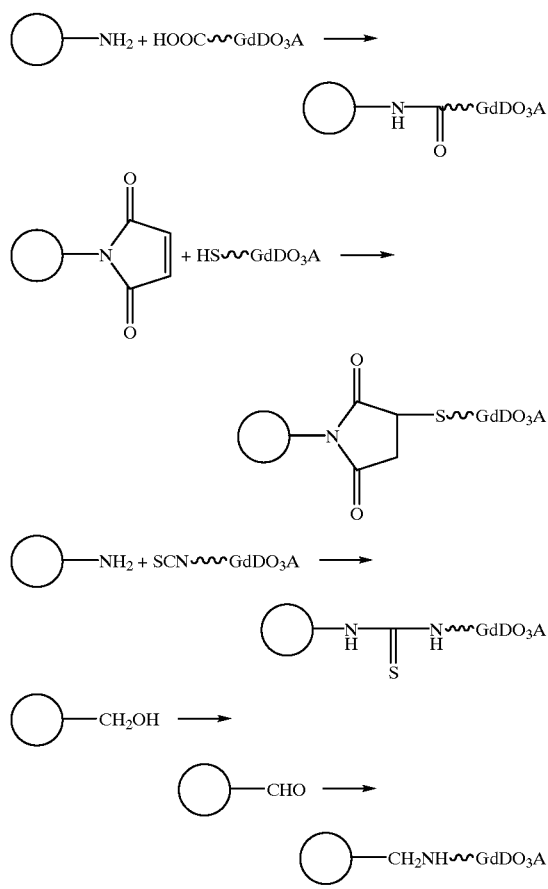

As an alternative to coupling chelates to anchor groups in the liposome, the anchor groups can be coupled to the chelate prior to liposome formation. The chelant is metallated in aqueous solution and then the chelate is coupled to the anchor molecule by conventional methods using a mixed solvent. The liposome is then formed using a lipid mixture including the chelate:anchor molecules. This avoids difficulties with non-specific binding of metal ions to liposomes which can occur when chelates are metallated in situ on the liposome surface as well as solubility problems associated with metallating water-insoluble chelants prior to liposome formation. The metal ions also serve as protecting groups during liposome formation for potentially active chelant groups.

In the finished liposome the chelate is tethered to the membrane surface by a lipophilic moiety (the anchor), e.g. a long alkyl chain or an aryl group, to which it is preferably attached by a biodegradable bond, e.g. an ester, carbamate, double ester, disulphide bond or phosphite ester.

Thus, for membrane tethered chelate moieties, compounds of formula III $$G—C''$$      III (where G is a lipophilic group, e.g. a long chain e.g. ($C_{10-20}$) alkyl group or an aryl group (e.g. phenyl or 5–7 membered heteroaryl), C'' is a metallated cyclic chelant group (e.g. a carboxyl group-carrying cyclopolyazaalkane group or a derivative thereof), and the G-C'' link preferably involves a biodegradable bond such as an ester, carbamate, double ester or disulphide bond) may be used. G conveniently represents a phospholipid group attached to C'' via an optionally biodegradable linker.

Double ester bonds, i.e. bonds of formula —O—CO—O—$CH_2$—O—CO—O— from which one or both of the terminal oxygens may be omitted and in which the methylene group may be substituted, are particularly suitable as biodegradable bonds.

Each liposome will preferably carry 10 to 50 mol % chelated metal ions (relative to the liposome membrane forming molecules) and this loading level may be selected by appropriate choice of the relative concentrations of the chelate and membrane forming moieties and of the liposome size.

The above discussion has concentrated on liposomes where the chelate is bound to the liposome surface. If desired, further chelate moiety, such as conventional water-soluble, low molecular weight chelates (for example, GdDTPA and GdDTPA-BMA), may be carried within the liposome interior.

The opsonization inhibitor may again generally be any of the types discussed above and may be provided with a lipophilic moiety, generally a hydrophobic end group as described above, to enable it to be tethered to the membrane surface. Each liposome will preferably carry 1 to 10 mol % (relative to the liposome membrane forming molecules) of such tethered opsonization inhibitors, generally making up 3 to 30 weight percent relative to the membrane forming material.

The third form of macrostructure mentioned above includes as a backbone structure a macromolecule such as an oligomeric, polymeric or dendrimeric polychelant, e.g. as described in WO-91/05792, WO-90/12050, WO-93/06868 and GB 9407812.8, the disclosures of which are incorporated herein by reference. In this embodiment the macromolecular skeleton serves to carry both the plurality of chelate moieties and a plurality of opsonization inhibitor moieties.

Dendrimeric polychelants such as described in WO-93/06868 are especially preferred as the backbone structures, particularly those where the overall molecular weight is in the range 2,000–20,000 D. In the production of such polychelants, chelant moieties are loaded onto the polymeric skeleton at a plurality of attachment sites. For the purposes of the invention, however, at least 3 such sites and preferably 2 to 50% of such sites will generally be loaded instead with opsonization inhibitor moieties.

Once again chelate and opsonization inhibitors moieties as discussed above may be used, the former preferably being attached via biodegradable bonds. Such biodegradable bonds may be at the chelant: macrostructure interface or may be so disposed within the polymer structure as to release chelate carrying fragments having molecular weights below the kidney threshold. For macromolecule:chelant and macromolecule: inhibitor conjugation to be effected, the macromolecule, chelant and inhibitor may need to be derivatised to provide appropriate attachment sites. This may be done by conventional means, e.g. by carbamate ester activation of monomethoxy-PEG to give nitrophenylcarbamate-PEG methoxy or by any of the means described for polychelant preparation in the MR field, e.g. in WO-90/12050 or GB 9407812.8.

The final category of agents according to the invention are the so-called particulates. This would include, for example, zeolites, e.g. as descirbed in WO-93/08846, which may act as a chemical/physical cage carrying the chelated diagnostic metal species. Such structures, however, will generally be of lesser interest for administration into the vasculature due to their eventual uptake by the RES system and the resultant likelihood that the chelated metals will have more prolonged bioretention. Nonetheless, such particulate chelate carriers can be conjugated to opsonization inhibitors, such as those discussed above, to provide contrast agents according to the invention. Where this is done, the particulate size (diameter) will preferably be in the range 20 to 1000 nm, especially 50 to 500 nm and loading levels will preferably be 2 to 20 weight % paramagnetic metal respectively.

In general, while at least 3 opsonization inhibitor moieties should be attached to each macrostructure in the agents of the invention, there is an optimum loading level above which opsonization inhibition is reduced and generally the inhibitor moieties will not account for more than 50% of the overall mass of the structure.

Viewed from a further aspect, the invention also provides a process for the preparation of the contrast agents of the invention, said process comprising (i) metallating a macrostructure which has bound thereto a plurality of opsonization inhibiting moieties and chelant groups; or (ii) binding a plurality of opsonization inhibiting moieties to a macrostructure which carries chelated ionic paramagnetic or heavy metal moieties; or (iii) generating a macrostructure from a plurality of molecular components which plurality of components includes opsonization inhibiting moieties and chelated ionic paramagnetic or heavy metal moieties.

In general, where the contrast agents of the invention comprise polychelant molecules, these may be synthesized by conjugating the chelant moieties to a backbone polymer molecule prior to conjugating the backbone polymer to any opsonization inhibitor such as PEG. The metal ions can be added to form the metal complex of the polychelants prior to or following conjugation of the polychelant to the inhibitor. Preferably, the metal will be added prior to conjugation of the polychelant to the inhibitor. However, for some metal ions such as radionuclides with a short half-life, metallation will preferably be performed following conjugation, just prior to use.

In general, known methods can be used to join the chelants to backbone molecules. See WO-90/12050. Such methods include for example the mixed anhydride procedure of Krejcarek et al. (Biochemical and Biophysical Research Communications 77:581 (1977)), the cyclic anhydride procedure of Hnatowich et al. (see Science 220:613 (1983) and elsewhere), the backbone derivatisation procedure of Meares et al. (see Anal. Biochem. 142:68 (1984)) and the method described by Manabe et al. in Biochemica et Biophysica Acta 883:460–467 (1986) for attaching DTPA residues onto a poly-L-lysine backbone using a modification of the cyclic anhydride procedure. While for preferred macrocyclic chelants, such as DOTA, the conventional mixed anhydride and cyclic anhydride conjugation techniques described by Krejcarek and Hnatowich are ineffective, it has been found that modifying the mixed anhydride procedure by reacting a polycarboxylic macrocyclic chelant in an anhydrous medium with an amine base of sufficient strength to abstract all the carboxyl protons (i.e. a high enough pKa) yields an amine salt which can react with an alkylhaloformate to produce an activated anhydride capable of conjugating to a backbone polyamine without causing the undesired cross-linking associated with prior art bifunctional polychelants. For most macrocyclic chelants tetramethylguanidine, or an amine base of similar strength, will be the preferred base.

More complex conjugation techniques, involving for example the use of backbone derivatized macrocyclic chelants in a manner analogous to that of Meares et al. (supra), may of course be used but the increased cost and complexity of the overall production makes this a less desirable route. Similarly the chelants can be attached to the backbone polymer by a haloacetylhalide, a phosgene or a thiophosgene method depending on the available reactive group on the chelating agent.

For chelants, eg. macrocycles, with a pendant carboxylate, including but not limited to DOTA, TETA, TRITA (1,4,7,10-tetraazacyclotridecanetetraacetic acid) and NOTA, one of the carboxylates can form an entity which can react with a primary amine group of the backbone polymer. Methods of forming a reactive entity from a carboxylate group include the modified mixed anhydride reaction for example using isobutylchloroformate (IBCF), or the formation of an "activated ester" using a carbodiimide (DCC or EDAC, cf. Pierce Catalog (1988), pages 252 and 253). Both reaction sequences give rise to a backbone polymer multiply substituted with the chelant moieties through stable amide linkages. The modified mixed anhydride method however is the preferred method for use in joining carboxylate containing macrocyclic chelants to the backbone polymer.

The modified mixed anhydride reaction is performed in an anhydrous solvent preferably with a melting point below 5° C., cooled to a temperature not lower than 5° C. or greater than about 55° C. above its freezing point. The solubilization of the chelant in the appropriate solvent is conveniently effected by preparation of the amine salt of the chelant using the amine base in situ.

The choice of base is determined by the pKa of the relevant carboxylates. For most chelants, tetramethylguanidine (TMG) is especially preferred. In general, bases will conveniently be selected from those bases whose pKa value exceeds the highest pKa of the chelant by at least 0.5, preferably 0.8, especially preferably at least 1.0. Amine bases having pKa's of at least 11, especially at least 11.3, particularly at least 12, are particularly preferred and besides TMG particular mention may be made of piperidine, quinuclidine and N-ethylpiperidine and more especially DBU (1,8-diazabicyclo[5.4.0]undec-7-ene) and DBN (1,5-diazabicyclo[4.3.0]non-5-ene). Further bases are listed by Martell and Smith in "Critical Stability Constants" Vol. 5, first supplement, Plenum Press, NY 1982.

The appropriate quantity of neat (chilled) alkylhaloformate is now added with stirring and the original temperature of the solvent is maintained by cooling, e.g. by addition of coolant, if required. Isobutylchloroformate is especially preferred. The resulting activated anhydride of the chelant can be reacted with an amine-containing dendrimer to form a magnifier polychelant. The magnifier polychelant, for most applications, is metallated at this point and purified by chromatography or crystallization to remove excess metal ions and lower molecular weight metal complexes. For use with target-specific molecules the magnifier polychelant, or the at least partially metallated form thereof, still containing at least one free amine, is conjugated to the targetting molecule, for example by reaction with one of many well-known heterobifunctional coupling agents. It is at this stage that loading with opsonization inhibitor may conveniently be effected. In situations where prior metallation is not appropriate, e.g. with radionuclide metal ions with short half-lives, the inhibitor: polychelant conjugate can be prepared using a metal-free polychelant and coupling as described above, followed by metallation (vide infra) and final rapid, simple purification by chromatography or filtration.

The chelants can also be linked to the backbone polymer through a non-coordinating primary amine group or a remote carboxyl group not involved in metal coordination. Macrocyclic chelants having a noncoordinating primary amine group include primary amine side-chain-derivatized DOTA macrocycles, primary amine derivatized D03A, and primary amine-derivatized hexaazasepulchrates and sarcophagines, as well as the broad class of derivatized crown ether cryptates. Where carboxyl groups on the chelant (or indeed on any other active moiety) are used for linkage, routine carboxyl activation chemistry can be used for attachment for example to amine functions on the backbone or on a linker conjugated to the backbone.

The non-coordinating primary amine group on these chelants can be reacted with a haloacetylhalide under well-known conditions to form a haloacetamide. The haloacetamide can react with a primary amine of the backbone polymer to form a stable amide linkage between the chelant and the polymer. The haloacetylhalide method described in De Riemer et al, J. Labelled Compd. Radiopharm. 18:1517 (1981) can be used to join amine containing chelants to the backbone polymer.

Amine groups on a chelant can also be reacted with phosgene or triphosgene to generate a reactive isocyanate group, or with thiophosgene to generate a reactive isothiocyanate group. Those groups can react with a primary amine of the backbone polymer to form a stable urea or more stable thiourea linkage, respectively, between the ligand and the backbone polymer. Gansow, Inorg. Chimica Acta 91:213 (1984) and Moi et al, J. Amer. Chem. Soc. 110:6266 (1988) describe methods of linking chelants to proteins having an amine group through formation of the isocyanate or isothiocyanate moieties using the phosgene or thiophosgene methods, respectively. See also Desreux, Inorg. Chem. 19:1319 (1980); Bryden et al, Anal. Chem 53:1418 (1981); Delgardo et al, Talanta 29:815 (1982); Cacheris et al, Inorg. Chem. 26:958 (1987); Moi et al, Inorg. Chem 26:3458 (1987) and Meares et al, Acc. Chem. Res. 17:202 (1984).

Still further means of coupling the chelant moieties to the backbone polymer are illustrated by the following reaction schemes:

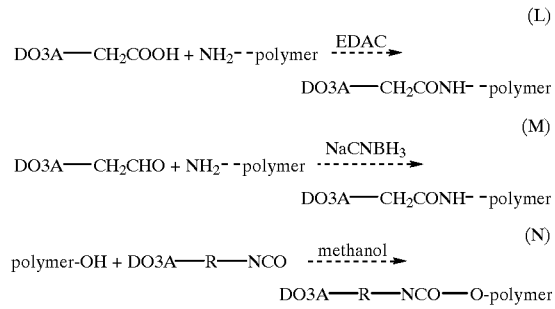

For amine terminating dendrimeric polymers the material $NH_2$—polymer represents a full generation (eg. $G_{2.0}$) dendrimer.

The interposition of an oligoamino acid (e.g. oligolysine) chain in the polymer to chelant (or inhibitor) moiety linkage is particularly desirable as this provides the capacity for controlled in vivo hydrolytic release of the attached moiety. (See "The Application of Drug Polymer Conjugates in Chemotherapy" by Hoes and Feijen in "Drug Carrier Systems" Roerlink et al Eds., J Wiley, 1989).

Metal ions are chosen for chelation in the blood pool agents of the invention for their ability to perform their diagnostic role. These roles include but are not limited to enhancing images in MRI, gamma scintigraphic or CT scanning, or X-ray.

Metals that can be incorporated, through chelation, include lanthanides and other metal ions, including isotopes and radioisotopes thereof, such as, for example, Mg, Ca, Sc, Ti, B, In, Cr, Mn, Fe, Co, Ni, Cu, Zn, Ga, Sr, Y, Sr, Tc, Ru, In, Hf, W, Re, Os, Pb and Bi. Particularly preferred radioisotopes of some of the foregoing include $^{153}$Sm, $^{64}$Cu, $^{67}$Cu, $^{67}$Ga, $^{68}$Ga, $^{89}$Sr, $^{88}$Y, $^{90}$Y, $^{99m}$Tc, $^{97}$Ru, $^{103}$Ru, $^{111}$In, $^{186}$Re, $^{188}$Re, $^{203}$Pb, $^{211}$Bi, $^{212}$Bi, $^{213}$Bi, and $^{214}$Bi. The choice of metal ion for chelation will be determined by the desired diagnostic application.

As mentioned, the choice of metal ions to be held in chelate complexes by the contrast agents of the invention depends upon the diagnostic technique for which the agent is to be used. For MRI and MRS, the metal ions should be paramagnetic, and preferably non-radioactive. For X-ray and ultrasound imaging, heavy metal ions, e.g. with atomic numbers of at least 37, preferably at least 50, should be used, again preferably non-radioactive species. For scintigraphy the metal ions should of course be ions of radioactive isotopes. For MR, X-ray, EIT or magnetometric imaging, one may use chelating groups to bind to heavy metal clusters (eg polyoxoanions and that full or partial sulphur analogues) or to iron oxides or other superparamagnetic polyatomic species.

For lipophilic macrostructures according to the invention metal incorporation is preferably accomplished prior to liposome formation.

For zeolite macrostructures, metal incorporation is preferably effected before conjugation of the opsonization inhibitors. Pore mouth engineering or surface dealumination as described in WO-93/08846 will also preferably be effected.

Methods of complexing metal ions with chelants and polychelants are within the level of skill in the art. Each of the metals used can be incorporated into a chelant moiety by one of three general methods: direct incorporation, template synthesis and/or transmetallation. Direct incorporation is preferred.

For direct metallation, the metal is titrated from substoichio metric levels up to full incorporation, thus eliminating the need for dialysis and extensive chromatographic purification. In this manner significant losses as well as dilution are avoided. Non-specific binding of the metal ions is also prevented. However, application of the invention to radionuclides with short half-lives may require metallation as a final step, followed by simple rapid purification (e.g. gel filtration) to remove excess unbound radionuclide.

The metal ions Fe(III), Cr(III), Mn(II), Hg(II), Pb(II), Bi(III) and the lanthanides can be directly incorporated into polyaminopolycarboxylates by the following general procedure. A water-soluble form of the metal, generally an inorganic salt, is dissolved in an appropriate volume of distilled, deionized water. The pH of the solution will be below 7. An aqueous solution containing an equimolar amount of the chelant is added to the metal solution at ambient temperature while stirring. The pH of the mixture is raised slowly by addition of base, typically 0.1 M NaOH, until the donor groups of the chelant are deprotonated, generally in the pH range of 5 to 9, depending on the chelant moieties. Particular care must be taken with the lanthanide ions to maintain the pH below 8 to avoid precipitation of the metal hydroxide. Metal incorporation into DOTA derived and related macrocyclic chelant moieties will normally be a slow process, as described in the references cited below. Specific examples of the procedure are contained in the following references.

Choppin et al, J. Inorg. Nucl. Chem., 33:127 (1971), Margerum, Rec. Chem. Prog., 24:237 (1973) and D'Olieslager et al, J. Inorg. Nucl. Chem., 35:4255 (1973) describe direct incorporation of the lanthanides into polyaminopolycarboxylates. Margerstadt, Mag. Res. Med., 3:808 (1986) and WO-A-87/06229 describe incorporation of Gd(III) into DOTA. A method of preparing Bi and Pb complexes of DOTA is described by Kumar et al, J. Chem. Soc. Chem. Commun., 31:145 (1989). The above references are incorporated herein by reference in their entirety.

Direct incorporation of Hf, Zr, W, Hg and Ta can be performed according to well known methods. See, for example, U.S. Pat. No. 4,176,173 (Winchell)

Transmetallation is useful when the metal ion needs to be reduced to a more appropriate oxidation state for the donor atoms of the chelant moiety to bind. For example, to incorporate $^{99m}$Tc or $^{186/188}$Re, the metal ion must be reduced to Tc(V) or Re(V) by the use of reducing agents such as $SnCl_2$ or cysteine by well known methods. This method requires formation of an intermediate complex. A typical example is the reduction of $^{99m}$Tc with Sn in the presence of a weakly coordinating ligand such as glucoheptonate prior to complexation with chelants such as DOTA. These methods are well known in the radiopharmaceutical art. $^{67}$Cu utilizes tetraamine chelates such as tet A or tet B (see Bhardaredj et al., JACS, 108:1351 (1986)) to stabilize Cu(II) for reaction with stronger-binding chelants.

The contrast agents of the invention may be administered to patients for imaging in amounts sufficient to yield the desired contrast with the particular imaging technique. Generally dosages of from 0.001 to 5.0 mmoles of chelated imaging metal ion per kilogram of patient bodyweight are effective to achieve adequate contrast enhancements. For most MRI applications preferred dosages of imaging metal ion will be in the range from 0.001 to 1.2, e.g. 0.01 to 0.5, mmoles/kg bodyweight while for X-ray applications dosages of from 0.5 to 1.5 mmoles/kg are generally effective to achieve X-ray attenuation. Preferred dosages for most X-ray applications are from 0.8 to 1.2 mmoles of the lanthanide or heavy metal/kg bodyweight.

For X-ray applications, to extend the photon energy range over which the contrast agents of the invention are optimally effective two or more different chelated metals may be used simultaneously.

There are many methods available for attachment of polyethyleneglycol or monomethylpolyethylene glycol to polyamines or other macrostructures. Attachment may for example be accomplished through an inert covalent linkage or through a biodegradable attachment (e.g. carbamate). The methodology for such attachment can be found in the following references: Harris, Rev. Macromol. Chem. Phys. C25(3):325 (1985), and Delgado, Critical Rev. Drug Carrier Sys. 9(3,4):249 (1992). Thus an exemplary scheme is as follows:

General Methods to Construct an Opsonization Inhibitor-loaded Compound:

$H_2N$—R is an amino group on a macrostructure (or a macrostructure component or on a group which can conjugate to a macrostructure, e.g. by incorporation within a liposome membrane or reaction with a surface group of a particulate) that may or may not have active moieties (e.g. metal chelates) already attached. MePEGX is methoxy terminated PEG of molecular weight 500–10,000.

Possible Routes Using PEG Attachment Chemistry

It should be noted that many activated PEG compounds suitable for use in the preparation of aggregate compositions according to the invention are available commercially, e.g. from Shearwater.

1. Cyanuric chloride route: Coupling conditions=pH 9, reaction with thiols, possible dimerization with mono derivative, UV chromophore.

Reactions:

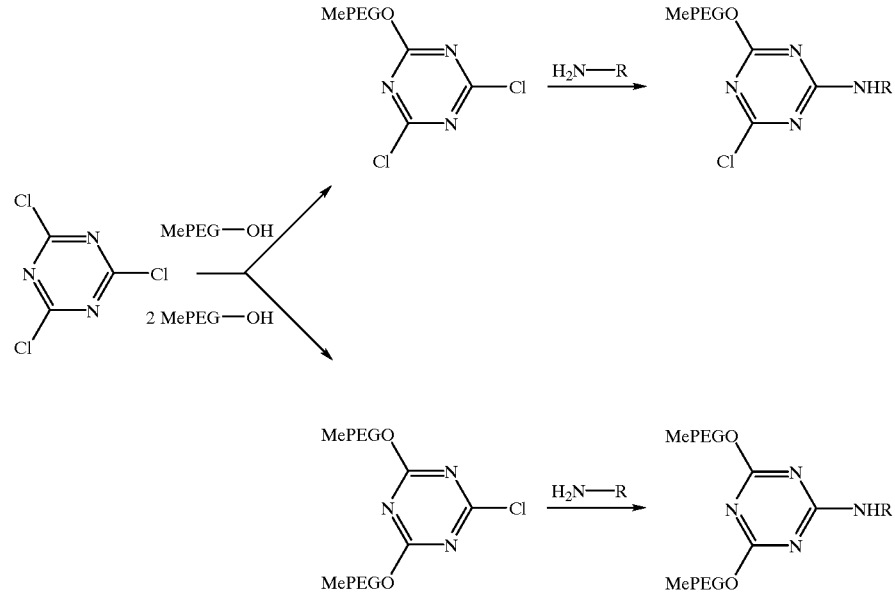

(see for example Anal. Biochem. 165:114 (1987) and J. Biol. Chem. 252:3582 (1977)).

2. Route leading to an Amide bond between PEG and magnifier: a macrostructure or macrostructure component unreactive with thiols, possible ester hydrolysis with succinic derivative.

Reactions:

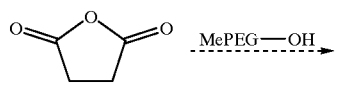

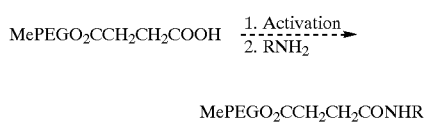

(see for example Appl. Biochem. Biotechnol. 11:141 (1985) and Cancer Biochem. Biophys. 7:175 (1984)).

3. Carbamate bond between PEG and a macrostructure or macrostructure component; Long reaction time, coupling conditions=pH 8.5–9.2, appreciable hydrolysis, activated PEG can be stored.

Reactions:

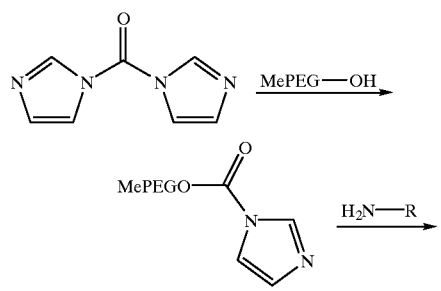

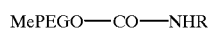

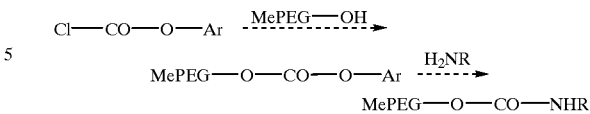

(see for example Klin. Paediatr. 200:184 (1988) and Anal. Biochem. 131:25 (1983)).

4. Attachment with sulfonyl chlorides: Mild conditions (pH 7.5, ambient temperature), rapid reaction Reactions:

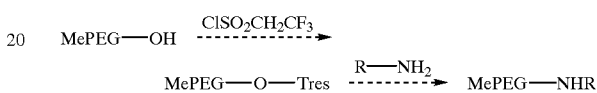

(see for example Biotechnol. Appl. Biochem. 12:119 (1990)).

5. Amine Linkage: Very stable linkage:

Reactions:

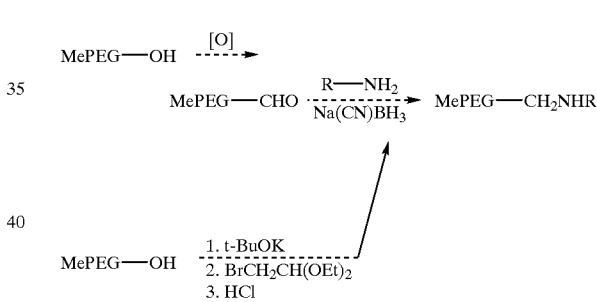

(See for example J. Macromol. Sci., Rev. Poly. Chem. Phys., C25:325 (1985) and J. Polymer Sci. 22:341 (1984)).

A) React PEG first          B) React DO3A first*

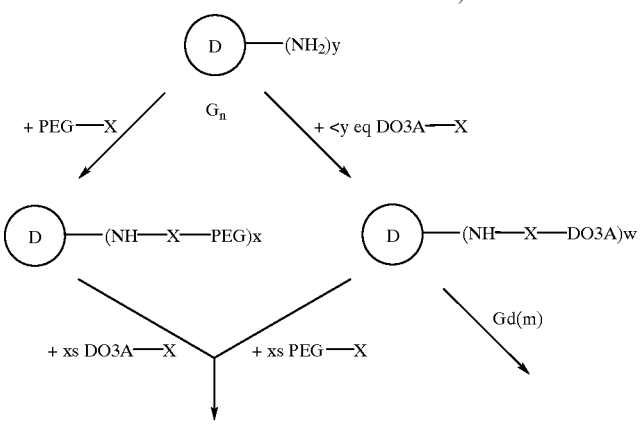

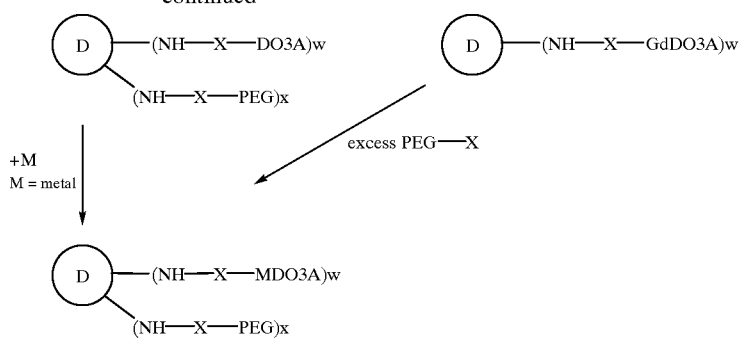

*Use less than stoichiometric of chelate (<y eq) to leave open sites for attachment of several PEG moieties.

D in the scheme above represents an nth generation, dendrimer reacted to load chelant and opsonisation inhibitor moieties thereon. n is generally low, eg up to 5.

Viewed from a further aspect therefore the invention provides a diagnostic contrast agent composition comprising a contrast agent according to the invention together with at least one physiologically tolerable carrier or excipient.

The contrast agents of the present invention may be formulated with conventional pharmaceutical or veterinary aids, for example emulsifiers, fatty acid esters, gelling agents, stabilizers, antioxidants, osmolality adjusting agents, buffers (e.g. tromethamine hydrochloride), preservatives, antimicrobial agents, pH adjusting agents, additions (e.g., 0.01 to 10 mole percent) of chelants (such as, for example, DTPA or DTPA bisamide), or calcium chelate complexes (as for example calcium DTPA or, CaNaDTPA-bisamide), or, optionally, additions (e.g., 1 to 50 mole percent) of calcium or sodium salts (for example, calcium chloride, calcium ascorbate, calcium gluconate or calcium lactate), etc., and may be in a form suitable for parenteral administration, for example injection or infusion directly or after dispersion in physiologically tolerable carrier media. Thus the contrast agent compositions of the present invention may be in conventional pharmaceutical administration forms such as powders, solutions, suspensions, dispersions, etc.; however, solutions, suspensions and dispersions in physiologically acceptable carrier media, for example water for injections, will generally be preferred.

The compositions according to the invention may therefore be formulated for administration using physiologically acceptable carriers or excipients in a manner fully within the skill of the art. For example, the contrast agents, optionally with the addition of pharmaceutically acceptable excipients, may be suspended or dissolved in an aqueous medium, with the resulting solution or suspension then being sterilized.

The parenterally administrable compositions according to the invention e.g., intravenous solutions, should be sterile and free from physiologically unacceptable agents, and should have low osmolality to minimize irritation or other adverse effects upon administration. Suitable vehicles include aqueous vehicles customarily used for administering parenteral solutions such as Sodium Chloride Injection, Ringer's Injection, Dextrose Injection, Dextrose and Sodium Chloride Injection, Lactated Ringer's Injection and other solutions such as are described in Remington's Pharmaceutical Sciences, 15th ed., Easton: Mack Publishing Co., pp. 1405–1412 and 1461–1487 (1975) and The National Formulary XIV, 14th ed. Washington: American Pharmaceutical Association (1975).

Viewed from a still further aspect the invention provides the use of a contrast agent according to the invention for the manufacture of a diagnostic composition.

Viewed from another aspect the invention provides a method of generating an image of a human or non-human animal, especially mammalian, body which method comprises administering into the systemic vasculature of said body an image enhancing amount of a contrast agent according to the invention or a salt thereof and thereafter generating an image e.g. an MR, X-ray, ultrasound, EIT or scintigraphic image, of at least a part of said body.

This invention is further illustrated by the following specific but non-limiting examples. Temperatures are given in degrees Celsius and concentrations as weight percentages unless otherwise specified.

EXAMPLE 1

Purified Extract from LaJolla Blue ZZ (LJBII)

a. Synthesis (i) Sulfonylation: Silicon phthalocyanine (5000 mg) is dissolved in fuming sulfuric acid (15 mL) and heated to 75° C. for 1 h. The reaction mixture is poured onto ice. The product is collected, washed with 1M HCl, and redissolved in 1M NaOH (2 mL). The insoluble impurities are removed by filtration and the filtrate is neutralized with 1 M HCl. The product is isolated and dried in vacuo.

(ii) PEGylation: One of the sulfonates above is modified by chlorination using $SOCl_2$ (32 mL at ambient temp.). The mixture is heated for 3 hours at 80° C. and cooled. About 4 mL of the mixture is added dropwise to ice and filtered, then dried in vacuo. PEG-ethanolamine (Avanti, average PEG= 2000; see also $H_2N$—PEG—OH. Huang et al. Polym. Sci., Polym. Chem. Ed., 13:795 (1985)) is dissolved in 10 mL of dichloromethane and added to the above solid in diisopropylethylamine (0.5 mL). After stirring for 20 hours, the solution is partially evaporated and 2 mL of toluene is added. The mixture is dried and purified as outlined below.

b. Purification of Crude Product

Crude LJBII was first filtered through a membrane filter in water (MWCO=10 KD): The retentate was evaporated and re-dissolved in dichloromethane and eluted from a silica gel column with a 2.5% to 50% methanol gradient in dichloromethane. The main peak was collected and analyzed for purity by HPLC (95.5% pure product, PKB-100 column, $MeOH/H_2O$, HOAc(0.48%) in ratios of 62.5/0.5/37, pH 7.1, 1.2 mL/min). Elemental analysis N/S ratio=9.75 to 10.5 indicating mono-sulfonate, monoamino-PEGylated silicon phthalocyanine. Mass Spec. (M+Na)+ at 2187.5 to 2980.4 corresponding to ethylene oxide chains of 31 to 49 units confirming the predicted structure.

c. Aggregation

At concentrations greater than 0.15 mg/mL in water, purified LJBII did not pass through a membrane filter of MWCO 30 KD, but did pass through 0.2 μm filter. This indicated a larger structure than just the monomeric unit (MW=2500).

d. Biodistribution

The biodistribution and excretion of purified La Jolla Blue II was determined in the adult male Swiss Webster mouse following intravenous administration. The compound was administered at a dose of 0.05 mmol/kg to 24 mice assigned in groups of 3. Animals were sacrificed at preselected times (3, 9, 15, 30 and 60 minutes, 4 and 24 hours and 7 days; groups 1 through 8, respectively) after administration. Urine and fecal samples were collected from animals in the groups 6, 7 and 8. Samples were taken of blood and peritoneal fluid and major organs (liver, spleen, kidneys, heart, lungs, brain and gall bladder) were excised, weighed and homogenized in detergent (0.01% Tween 20). Aliquots of these semi-solubilized suspensions were measured for the presence of silicon phthalocyanine either with fluorimeter or by UV-visible absorption spectrophotometry. The concentration of compound was determined from standard curves for each of the tissues, prepared under identical conditions, from an untreated animal.

Blood levels averaged 15.71%±2.43 (S.D.) of the administered dose at 3 minutes after administration, 12.64%±3.39 at 4 hours, 2.79%±0.14 at 24 hours, and less than 1% (0.05%±0.00) at 7 days. The liver averaged 2.41%±0.82 of the administered dose at 3 minutes and did not change significantly during the 7 days of the study. The lung and kidney averaged 1.09%±0.20 (at 60 minutes) and 1.37%±0.11 (at 3 minutes), respectively, but were reduced to approximately 1% or less at 15 minutes. Cumulative recovery of La Jolla Blue II in the urine at 2 hours averaged 45.52%±4.92 (n=8) and approximately 76% (n=6) at 24 hours. After 7 days, 78.01%±10.10 (n=3) of the administered La Jolla Blue II was recovered in urine, with less than 1% accounted for in feces.

Purified La Jolla Blue II exhibited a biodistribution and excretion pattern more consistent with that of a blood pool agent than an extracellular fluid agent. Because the compound was detectable by fluorescence for up to 7 days, this suggests that there was no significant in vivo metabolism of the ring structure of the compound.

EXAMPLE 2

Amphoteric Gd-D03A Complex

Preparation of GdAE-D03A based amphoteric agent: a) 1,4,7 Tri-tertbutoxycarbonylmethyl-10-methoxycarbonylmethyl-1,4,7,10-tetraazacyclododecane (1a): 1,4,7-Tri-tertbutoxycarbonylmethyl-1,4,7,10-tetraazacyclododecane hydrobromide (25.0 g, 42 mmol) was slurried in acetonitrile and treated with TMG (70 mL). Methyl bromoacetate (6.5 g, 42 mmol) was added in one portion and the mixture was refluxed for 3 h. After stirring at ambient temperature for an additional 18 h, the solvent and excess TMG were removed by rotary evaporation. The residue was dissolved in $CHCl_3$, washed with water and dried ($Na_2SO_4$). Evaporation of the solvent afforded the title product as a pale oil (23 g, 95%).

$^1$H NMR($CDCl_3$) 1.4 (s,27H) , 2.8(s, 16H) , 3.2(s,6H), 3.4(s,2H), 3.6(s,3H)

b) 1,4,7-Tri-tertbutoxycarbonylmethyl-10-(N-(2 aminoethyl)amidomethyl)-1,4,7,10-tetraazacyclododecane (1b): Methyl ester 1a (23.0 g, 40 mmol) was dissolved in methanol (500 mL) and treated with ethylenediamine (200 mL). The mixture was stirred at ambient temperature for 3 d. The solvent and excess ethylenediamine were removed by rotary evaporation and the residue was dissolved in choloroform, washed with water, and dried ($Na_2SO_4$). The solvent was evaporated to yield the title product as a viscous oil (18 g, 75%).

$^1$H NMR ($CDCl_3$): 1.4 (s, 27H) , 2.5–3.0 (m,20H) , 3.3 (m,8H) , 6.0 (br s, 1H).

c) 1,4,7-Tri(carboxymethyl)-10-(N-(2-aminoethyl) amidomethyl)-1,4,7,10-tetraazacyclododecane (1c or AE-D03A): Ester (1b) (10.0 g, 16 mmol) was deprotected by reaction with neat TFA(200 mL) at ambient temperature for 3 h. After removal of the TFA, the residue was dissolved in 1 M NaOH and loaded on an ion exchange column ([AG 1×8 (OH—)], 200 mL). The column was washed with water and the product was eluted with 1.5 M HOAc. Concentration of the fractions containing the title product yielded 7.0 g (93%) as a white solid.

$^1$H NMR ($D_2O$): 2.9–3.6 (br mult.) Anal. Calcd. for $C_{18}H_{34}N_6O_7$·HOAc: C, 47.14; H, 8.11; N, 16.49. Found: C, 47.40; H, 7.98; N, 16.48.

d) 1,4,7-Tri(carboxymethyl)-10-(N-(2-aminoethyl) amidomethyl)-1,4,7,10-tetraazacyclododecane Gadolinium (III) (1d): The ligand (1c or AE-D03A) (1 g) was dissolved in water and the pH adjusted to 5 with HCl. To the solution was added 1.0 equivalent of Gd (acetate)$_3$ with stirring. After several hours, the pH was adjusted to 6 and the solution was heated to 45° C. for a few hours. An aliquot was removed and tested for free Gd3+ by the xylenol orange test (negative). The solid was isolated after removal of the aqueous solution. The crude material was triturated with boiling ethanol and filtered hot to remove salts. Yield 95%.

e) GdAE-D03A-N-octadecyl

The complex from (1d) is dissolved in DMF and treated with octadecyl-bromide (Aldrich, 1.0 equivalent). After stirring at ambient temperature for 24 hours, the DMF is evaporated under reduced pressure. The residue is dissolved in chloroform and washed with water. The organic extracts are dried ($Na_2SO_4$) and evaporated to afford 1,4,7-tri (carboxymethyl)-10-(N-(octadecyl)-N-(2-aminoethyl) amidomethyl)-1,4,7,10-tetraazacyclododecane Gadolinium (III) (1e)

f) GdAE-D03A-N-octadecyl-N-PEG5000

The compound from (1e) is dissolved in chloroform and treated with 1.1 equivalents of triethylamine and 1.0 equivalent of methoxy-succinal-PEG5000 (Shearwater Corp.). After stirring at ambient temperature for 24 hours, the reaction mixture is washed with water, dried and concentrated by rotary evaporation. The crude product is recrystallized from ethanol/isopropanol/water.

EXAMPLE 3

Amine-core Dendrimer Based Agent

A)Preparation of Generation 4 Dendrimer

The same procedure was followed as in Watson (WO-93/ 06868) to generate a Generation 4.0 dendrimer. $G_4$(0.56 g) was dissolved in d.i. $H_2O$ (20 mL) and in a separate flask, D03A-bz-NCS (2.31 g, 20% excess prepared as described in GB 9407812.8) was dissolved in $H_2O$ (80 mL) and the pH adjusted with 5N NaOH to 8.5. The latter solution was slowly added (small aliquots) to the dendrimeric solution with vigorous stirring. The addition was complete within 10 min. After stirring for four days, the solution was passed through a medium porosity frit and the volatiles removed by roto-evaporation (heat setting 60). 0.48 g of the light orange solid was taken and filtered using Centriprep C-10 filter. This was shown by GPC to effectively separate the low molecular weight impurities from the desired product. The rest of the crude mixture was filtered in this manner and a total of 2.1 g of product was isolated. Integration of the $^1$H NMR spectrum gave an approximate average loading of 30 chelates per dendrimer (y=30) for a 63% loading efficiency. The product was also characterized by $^{13}$C NMR and CZE analysis.

B) Gadolinium Incorporation:

Product from step A (551 mg) was dissolved in d.i. $H_2O$ (11 mL) while Gd $(OAc)_3 \cdot 4H_2O$ (0.90 g) was dissolved in 8 mL of $H_2O$. The dendrimer solution was added to the latter since not all of the gadolinium acetate had solubilized. Additional $H_2O$ was added (10 mL) and pH checked (5.0). After 24 hours at ambient temperature, the solution was heated to 45° C. for 3.5 hours. The resulting solution was filtered (2×45 min) using Centriprep C-10 filters to remove most of the unreacted gadolinium salts. The pH of the resulting solution was raised to 9 to precipitate any unreacted gadolinium as $Gd(OH)_3$ and filtered through a 0.45 μm filter. A Xylenol Orange test was negative for free gadolinium. Removal of chloride salts was by ultrafiltration, and was monitored by GPC. This resulted in the formation of a pure product (about 300 mg).

C) PEGylation

The product from step B, $G_4(N[CS]N$-bz-D03A$)_{30}$ (160 mg, 5.3×10$^{-6}$ mol), and PEG-NPC (nitrophenylcarbamate) 5000 (480 mg, 9.6×10$^{-5}$ mol, Shearwater Chemical SPA) are placed in separate flasks to which deionized water is added (10 mL, respectively). The slightly cloudy PEG solution is added rapidly to $G_4(N[CS]N$-bz-D03A$)_{30}$ and the resulting solution (pH 7.8) is stirred at ambient temperature for 24 hours. The solution is purified using ultrafiltration (Centriprep C-10 and C-30). TLC (MeOH/CHCl$_3$, 1:1) shows removal of PEG species to be efficient. The product is characterized by conventional spectroscopic methods (NMR, IR, UV) and light scattering (LALLS, PCS). Alternatively, the product is purified using G-50 Sephadex chromatography.

EXAMPLE 4

Dendrimer Based Agent (a) Synthesis of $P_{G2}(D03A)_{10}$ $P_{G2}(NH_2)_{24}$(250 mg, 0.05 mmol) (prepared as described in GB9407812.8) was dissolved in H2O (15 mL) and the pH noted (10.1). In a separate flask was placed D03A-bz-NCS NCS(750 mg, 1.18 mol, 23.6 eq) dissolved in $H_2O$ (40 mL). The pH was raised from 2.1 to 7.0 with 1 N NaOH. The $P_{G2}$ solution was added to the chelate rapidly and the pH noted. (8.0). The slightly cloudy yellow solution was stirred for six hours at which time it was filtered (0.2 μm) and the resulting clear yellow solution concentrated to 30 mL. The concentrate was then placed into four C-3 Centriprep units and ultrafiltered (3×60 min). The retentates were combined and stripped to give the title product as a light yellow solid (610 mg). Elemental analysis indicated the presence of some unreacted chelate. NMR and a fluorescence amine assay indicated that 10 of the 24 sites had been modified.

(b) Synthesis of $PG_2(GdD03A)_{10}$ $P_{G2}(D03A)_{10}$(560 mg, 0.333 mmol) and Gd(OAc)$_3$(410 mg, 1.22 mmol) were placed in separate flasks and dissolved each in $H_2O$ (20 and 10 mL, respectively). The Gd was added to dendrimer and the pH adjusted to 5.5 with 1 N NaOH. The pH was monitored every 2 hours. After stirring the solution was concentrated and the excess Gd was removed via exhaustive ultrafiltration (C-3 units, 7×40 min). At this time a xylenol orange test was negative. The title product was isolated as a light yellow solid (270 mg). Low angle laser light scattering (LALLS) and florescence spectroscopy determined the chelate loading to be 10. The product was taken forward to the next step, PEGylation.

(c) Synthesis of $P_{G2}$ (GdD03A)$_{10}$(PEG$_{2000}$)$_{14}$ $P_{G2}$(GdD03A)$_{10}$(270 mg, 2.35×10$^{-5}$ mol) was dissolved in borate buffer pH 8.7, 80 mL). This solution was added rapidly into a separate flask which contained solid PEG$_{2000}$-NPC (0.89 g, 4.49×10$^{-4}$ mol, 20 eq). The solution turned bright yellow immediately (presence of p-nitrophenol). After stirring for 18 hours, the solution was concentrated and run down a Sephadex G-25 column to remove nitrophenol and salts. Excess PEG was removed by dialysis (Sigma 12 kD tubing) against borate buffer (pH 9). LALLS indicated the presence of a species corresponding to a MW of 4000 along with the product at MW 30 kD.

Characterization of the product was carried out by a number of methods. LALLS indicated a MW of 31 kD at loading of 10 or 11 PEG molecules. Fluorescence spectroscopy indicated full loading of the terminal amine groups, i.e. 14 PEG molecules attached. Elemental analysis suggested full loading of PEG also. The product, which was isolated as a yellow solid (410 mg) was identified as $P_{G2}$(GdD03A)$_{10}$ (PEG$_{2000}$)$_{14}$. Relaxivity (water, 20 MHz) $r_1$=13.7 mM$^{-1}$s$^{-1}$.

EXAMPLE 5

Scale up of $G_3$(GdD03A)$_{10}$(PEG$_{2000}$)$_9$.

(a) Preparation of $G_3(N[CS]N$-bz-D03A$)_{10}$.

The previously developed procedure was employed with the starting materials $G_3$ (400 mg, 7.97×10$^{-5}$ mol) (see GB9407812.8) and D03A-bz-NCS (1.48 g, 2.3 mmol). The product was isolated as a yellow solid (1.44 g). $^1$H NMR integration showed the loading to be 10 chelates out of 24 terminal amine sites.

(b) Preparation of $G_3(N[CS]N$-bz-D03A$)_{10}$

Conventional synthetic methods were used with $G_3(N[CS]N$-bz-D03A$)_{10}$(1.33 g) and Gd(OAc)$_3 \cdot 3H_2O$. The title product was isolated as a pale yellow solid (760 mg). Light scattering and fluorescence indicated the presence of 10 chelates, in agreement with the previous result. The balance of the material was carried forward to the next step.

(c) Preparation of Scale up of $G_3$(GdD03A)$_{10}$PEG$_{2000}$)

(i) The reaction was initially tried on a small scale with 100 mg $G_3$(GdD03A)$_{10}$ and 220 mg PEG$_{2000}$-NPC. The product was worked up in a similar fashion as described above to give the product as a off-white solid (140 mg).

(ii) The procedure described above for $P_{G2}$(GdD03A)$_{10}$ (PEG$_{2000}$)$_{14}$ was again used here with the amounts: $G_3$(GdD03A)$_{10}$ (650 mg) and PEG$_{2000}$-NPC (2.1 g). The product was isolated as a off-white solid (750 mg) and characterized using LALLS, florescence, ICP (Gd) and water analysis. All were in agreement with the assigned structure. A PEG loading of 13.8 was identified by fluorescence assay of terminal amines. Relaxivity (water, 20 MHz) $r_1$=13.7 mM$^{-1}$s$^{-1}$.

EXAMPLE 6

Synthesis of $G_3$(GdD03A)$_{10}$(PEG$_{5000}$)x $G_3$(GdD03A)$_{10}$(100 mg) and PEG$_{5000}$-NPC (0.615, ca 15 eq) were combined as described above. The product was isolated as an off-white solid (530 mg). Fluorescence spectroscopy indicated the reaction was highly efficient with PEG occupying the 14 remaining amine sites. TLC indicated the prescence of free unreacted PEG while LALLS indicated the PEG had dimerized with a molecular weight of 10000. A PEG loading of 11.3 was identified by assay. Relaxivity (water, 20 MHz) $r_1$=15.8 mM$^{-1}$s$^{-1}$.

EXAMPLE 7

1,4,7-Tri-tertbutoxycarbonylmethyl-10-methoxycarbonylmethyl-1,4,7,10-tetraazacyclododecane 1,4,7-Tri-tertbutoxycarbonylmethyl-1,4,7,10-tetraazacyclododecane hydrobromide (25.0 g, 42 mmol) was slurried in acetonitrile and treated with TMG (70 mL). Methyl bromoacetate (6.5 g, 42 mmol) was added in one portion, and the mixture was refluxed for 3 hours. After stirring at ambient temperature for an additional 18 hours, the solvent and excess TMG were removed by rotary evaporation. The residue was dissolved in CHCl$_3$, washed with water, and dried (Na$_2$SO$_4$). Evaporation of the solvent afforded the title product as a pale oil (23 g, 95%). $^1$H NMR (CDCl$_3$): 1.4 (s, 27 H), 2.8 (s, 16 H), 3.2 (s, 6 H), 3.4 (s 2 H), 3.6 (s, 3 H).

EXAMPLE 8

1,4,7-Tri-tertbutoxycarbonylmethyl-10-(N-(2-aminoethyl)-amidomethyl-1.4,7.10-tetraazacyclododecane The methyl ester of Example 7 (23.0 g, 40 mmol) was dissolved in methanol (500 mL) and treated with ethylenediamine (200 mL). The mixture was stirred at ambient temperature for 3 days. The solvent and excess ethylenediamine were removed by rotary evaporation, and the residue was dissolved in chloroform, washed with water, and dried (Na$_2$SO$_4$). The solvent was evaporated to yield the title product as a viscous oil (18 g, 75%). $^1$H NMR (CDCl$_3$): δ 1.4 (s, 27 H), 2.5–3.0 (m, 20 H), 3.3 (m, 8 H), 6.0 (br s, 1 H).

EXAMPLE 9

1,4,7-Tri(carboxymethyl)-10-(N-(2-aminoethyl) amido-methyl)-1,4,7,10-tetraazacyclododecane [GdAE-D03A]

The ester of Example 8 (10.0 g, 16 mmol) was deprotected by reaction with neat TFA (200 mL) at ambient temperature for 3 hours. After removal of the TFA, the residue was dissolved in 1 M NaOH and loaded on an ion exchange column [AG 1×8 (OH—), 200 mL]. The column was washed with water and the product was eluted with 1.5 M HOAc. Concentration of the fractions containing the title product yielded 7.0 g (93%) as a white solid. $^1$H NMR (D$_2$O): δ 2.9–3.6 (br mult.) Anal. Calcd. for C$_{18}$H$_{34}$N$_6$O$_7$ HOAc:C, 47.14; H, 8.11; N, 16.49. Found: C, 47.40; H, 7.98; N, 16.48.

EXAMPLE 10

1,4,7-Tri(carboxymethyl)-10-(N-(2-aminoethyl) amidomethyl)-1,4,7,10-tetraazacyclododecane Gadolinium (III)

The compound of Example 9 (1.0 g, 2.38 mmol) was dissolved in water (37 mL). The pH was adjusted to 5 by the addition of 1 M NaOH. Gadolinium (III) acetate was added in small portions until a slight excess of metal (by xylenol orange) was present. During the addition the pH was maintained at 5–6. The reaction mixture was stirred overnight at ambient temperature. Ligand (50 mg) was added and stirring was continued until a negative xylenol orange test was obtained. The water was removed under vacuum. The residue was chromatographed on Sephadex G-10 to remove inorganic salts. The fractions were analyzed by MS (FAB): MH$^+$=602.

EXAMPLE 11

1,4,7-Tri(carboxymethyl)-10-(N-(2-aminoethyl) amidomethyl)-1,4,7,10-tetraazacyclododecane-N-hemisuccinamide The compound of Example 9 (6.1 g, 13.6 mmol) in pyridine (20 mL) was heated until dissolution was complete. Succinic anhydride (1.5 g, 15 mmol) was added, and the mixture was heated for 1 hour. The solution was cooled and acetone was added to precipitate the product. The white solid was washed thoroughly with acetone and dried under vacuum to afford 5.0 g of the title product (67%).

EXAMPLE 12

1,4,7-Tri(carboxymethyl)-10-(N-(2-aminoethyl) amidomethyl)-1,4,7,10-tetraazacyclododecane-N-hemisuccinamide Gadolinium (III)

(A) The compound of Example 11 (1.9 g, 3 mmol) was dissolved in water (30 mL). The pH was adjusted with 1 N NaOH to 5.0. Gadolinium (III) chloride (~1.4/10 mL) in water was added dropwise until a slight excess of metal remained for several hours. Additional gadolinium (50 mg) was added, and the reaction mixture was stirred until a negative xylenol orange test was obtained. The water was evaporated, and the residue was chased several times with ethanol. The title product was purified by revese phase (C$_{18}$) preparative HPLC with 2% methanol in water as the mobile phase.

(B) The title compound was also prepared by an alternate procedure: The compound of Example 9 (240 mg, 0.4 mmol) in DMSO (10 mL) was heated at 80° until dissolution was complete. Succinic anhydride (40 mg, 0.4 mmol) was added and the mixture was heated for 6 hours. After cooling to ambient temperature, acetone was added to precipitate the title product. The white powder was washed with acetone and dried under vacuum. MS (FAB): MH$^+$683.2, MNa$^+$ 705.1.

EXAMPLE 13

13-Cholesteryl-3,6,9,12-tetraoxa-dodecan-1-ol

Cholesterol tosylate (2.0 g, 3.7 mmol) and tetraethyleneglycol (6.42 mL, 37 mmol) were dissolved in dioxane (100 mL) and heated at 70° C. for 6 hours. The solvent was evaporated, and the residue was dissolved in toluene and washed thoroughly with water. The organic layer was dried (Na$_2$SO$_4$), and concentrated to an oil. The crude material was purified by chromatography on a short column of silica with gradient elution of 0–20% methanol in chloroform to afford 1.0 g (49%) of the title product as a pale oil.

EXAMPLE 14

13-Cholesteryl-3,6,9,12-tetraoxa-dodecan-1-oic acid

The compound of Example 13 (0.5 g) in acetone (20 mL) was oxidized by the dropwise addition of Jones reagent until a slight excess was present. The reaction mixture was treated with isopropanol and was filtered through a plug of silica gel. The crude title product was pure by TLC and NMR.

EXAMPLE 15

GdD03A-stearyl amide

The compound of Example 9 (100 mg, 1.6 nmol) was dissolved in DMSO (10 mL) and was treated with stearoyl chloride (51 mg, 1.6 mmol). The reaction mixture was heated at 60° for 2 hours, and stirred overnight at ambient temperature. Water was added (50 mL) and the product was extracted into choloroform (3×100). The extracts were dried, and concentrated to afford the title product as a white solid. MS (FAB) 868.5 MH$^+$.

EXAMPLE 16

GdAE-D03A cholestearyl carbamate

The compound of Example 9 (300 mg, 0.8 mmol) was dissolved in DMSO (20 mL) and treated with cholesterol chloroformate (225 mg, 0.5 mmol). The reaction mixture was heated at 80° for 5 hours. The mixture was allowed to stand at ambient temperature until colorless cyrstals were deposited. MS (FAB) : MH$^+$1014.5, MNa$^+$1036.5.

EXAMPLE 17

LaD03A-succinyl-PE

LaD03A-Succinamide (130 mg, 0.2 mmol) was dissolved in DMSO (3 mL). Dicyclohexylcarbodiimide (39 mg, 0.2 mmol) was added followed by N-hydroxysuccinimide (22 mg, 0.2 mmole). The reaction mixture was stirred at ambient temperature for 1 hour, and PE (130 mg, 0.2 mmol) in chloroform (20 mL) was added. After 6 hours, the reaction mixture was filtered, washed with water, dried, and evaporated to yield the title product. TLC (65 CHCl$_3$/25 MeOH/4 H$_2$O/1 formic acid) R$_f$=0.2. MS (FAB): MH$^+$1400.7, MNa$^+$1422.7.

EXAMPLE 18

GdAE-D03A-glutaryl-PE

Egg PE-glutaryl (100 mg, 0.11 mmol) in chloroform (5 mL) was treated with N-hydroxysuccinimide (25 mg, 0.21 mmol) and dicyclohexylcarbodiimide (50 mg, 20.25 mmol). The reaction mixture was stirred at ambient temperature overnight and filtered to remove the urea. The compound of Example 10 (100 mg, 0.16 mmol) in methanol (1 mL) and 1 mL triethylamine were added. The reaction was stirred at ambient temperature for 6 hours, and evaporated to dryness. The residue was dissolved in chloroform (10 mL) and placed in a dialysis sac. The reaction was dialysed against sodium acetate buffer (1 L, 50 mM, pH 5.5, 12 hours), Tris buffer (1 L, pH 8, 50 mM, 5 hours), and deionized water (1 L, 5 hours). A small amount of precipitate which had formed in the chloroform layer was dissolved by the addition of methanol. The solution was dried (Na$_2$SO$_4$) and evaporated to yield the title product as a white, waxy solid (150 mg, 89%). TLC (65 CHCl$_3$/25 MeOH/4 H$_2$O/1 formic acid) R$_f$=0.2. MS (FAB) : MNa$^+$1459.

EXAMPLE 19

A mixture of Egg PC (52 μmole) and Egg PE-glutaryl (48 μmole) in chloroform was evaporated to a thin film under vacuum. The lipid mixture was dissolved in diethyl ether (3 mL) and treated with 23 mL buffer (25 mM MES, 100 mM NaCl). An emulsion was formed by sonication of the mixture. The ether was evaporated to form a gel. The gel was collapsed by vortexing and evaporation of the residual solvent. An additional 1 mL of buffer was added and evaporation was continued until all traces of solvent were removed. The liposomes were treated with GdAE-D03A (140 mg) and EDAC (130 mg) overnight at ambient temperature with rapid stirring. Unreacted reagents were removed by passing the product through a Sephadex G-75 column (1×8 in). The liposomes were extruded three times through two 100 nm membrane. Analysis of the final mixture gave [Gd]=1.14 mM, [P]=5.04 mM. Based on the P/Gd ratio, 47.1% of the PE-glutaryl was derivatized. Relaxivity (water, 20 MHz) r$_1$=18±2 (mMsec)$^{-1}$.

EXAMPLE 20

The same procedure described for the synthesis of Example 19 was used. Egg PC (20 μmole) and dioleoyl PE-succinyl (17 μmole). Analysis of the final mixture gave [Gd]=0.56 mM, [P]=3.8 mM. Based on the P/Gd ratio, 30% of the PE-glutaryl was derivatized. Relaxivity (water, 20 MHz) r$_1$=18±2 (mMsec)$^{-1}$.

EXAMPLE 21

The same procedure described for the synthesis of Example 19 was used. Egg PC (10 μmole) and dioleoyl PE-dodecanoyl (8 μmole) were used. The liposomes were extruded (3×200 nm, 3×50 nm). Analysis of the final mixture gave [Gd]=0.66 mM, [P]=3.49 mM. Based on the P/Gd ratio, 43% of the PE-glutaryl was derivatized. Relaxivity (water, 20 MHz) r$_1$=17±2 (mMsec)$^{-1}$.

EXAMPLE 22

The same method used to prepare Example 19 was used for a mixture of Egg PC (56 μmole) and Egg PE (53 μmole). The liposomes were treated with EDAC (100 mg) and GdAE-D03A-succinamide (80 mg) overnight at ambient temperature with rapid stirring. After removal of the unreacted reagent, the liposomes were extruded (3×200 nm and 3×50 nm). Analysis of the final mixture gave [Gd]=0.39 mM, [P]=5.87 mM. Based on the P/Gd ratio, 14% of the PE-glutaryl was derivatized. Relaxivity (water, 20 MHz) r$_1$=27±2 (mMsec)$^{-1}$.

EXAMPLE 23

Liposomes were prepared from Egg PC (13 μmole) and cholesterol hemisuccinate (16 μmole) by the same method used to prepare Example 19. The liposomes were treated with EDAC (25 mg) and GdAE-D03A (25 mg). After removal of the unreacted reagents, the liposomes were extruded (3×200 nm and 3×50 nm). Analysis of the final mixture gave [Gd]=0.26 mM, [P]=2.93 mM. Based on the P/Gd ratio, 7.2% of the PE-glutaryl was derivatized. Relaxivity (water, 20 MHz) r$_1$=21±2 (mMsec)$^{-1}$.

EXAMPLE 24

Liposomes were prepared from Egg PC (80 μmole) and 6-(cholesteryl)-7-oxaheptan-1-ol (80 μmole) by the method described for preparation of Example 19. The liposomes were treated with EDAC (70 mg) and GdAE-D03A (40 mg). After removal of the unreacted agents, the liposomes were extruded (3×200 nm and 3×50 nm) . Analysis of the final mixture gave [Gd]=0.39 mM, [P]=3.34 mM. Based on the P/Gd ratio, 11% of the PE-glutaryl was derivatized. Relaxivity (water, 20 MHz) r$_1$=19±2 (mMsec)$^{-1}$.

EXAMPLE 25

Liposomes were prepared from Egg PC (68 μmole), Egg PE-glutaryl (55 μmole) and Brain PS (6 μmole) by the method described for preparation of Example 19. The liposomes were treated with GdAE-D03A (40 mg) and EDAC (75 mg). After removal of the unreacted reagents, the liposomes were extruded (3×200 nm and 3×100 nm). Analysis of the final mixture gave [Gd]=0.51 mM, [P]=4.15 MM. Based on the P/Gd ratio, 29% of the PE-glutaryl was derivatized. Relaxivity (water, 20 MHz) $r_1$=18±2 (mMsec)$^{-1}$.

EXAMPLE 26

Liposomes are prepared by the method described for the synthesis of Example 19 from cholesterol hemisebacate (130 μmole) and Egg PC (130 μmole). The liposomes are treated with GdAE-D03A (120 mg) and EDAC (120 mg). Unreacted reagents are removed by gel chromatography and the liposomes are extruded.

EXAMPLE 27

The compound of Example 16 (71 mg, 6 μmole) was added to dioleolyl PC (15 mg, 20 μmole) in chloroform. The solvent was evaporated under vacuum. The residue was dissolved in ether (1 mL). Water (1 mL) was added, and the mixture was sonicated until an emulsion was formed. The ether was slowly evaporated under vacuum. A thick gel formed. Additional water (1 mL) was added and the gel was vortexed until the gel collapsed to form vesicles. The product was extruded (3×200 nm, 3×50 nm).

EXAMPLE 28

The compound of Example 18 (25 mg, 17.4 μmole) and Egg PC (13.7, 18 μmole) were dissolved in chloroform (3 mL). The solution was evaporated to dryness under vacuum. The residue was dissolved in ether (3 mL) and filtered. MES buffer (3 mL) was added and the mixture was sonicated until an emulsion formed. The ether was removed by evaporation under vacuum with occasional vortexing.

EXAMPLE 29

The compound of Example 15 (50 μmole) and hydrogenated Egg PC (150 μmole) are dissolved in a mixture of chloroform (10 mL) and methanol (2 mL). . The solvent is evaporated at 75°. The residual thin film is hydrated in MES buffer at 75° by shaking. After freeze-thawing four times, the liposomes are extruded (3×100 nm) at 75°.

EXAMPLE 30

Pharmacokinetics

A catheter was inserted into the jugular vein of a rat days prior to the study. A 300 μL sample of blood was drawn and placed in a tared tube containing heparin prior to injection of the sample. The test compound was injected at time zero. Blood samples (300 μL) were taken at intervals over a 24 hour time period. At 7 days the animal was sacrificed, and the liver spleen, and kidneys were removed. Blood and organ samples were digested with nitric acid and hydrogen peroxide and anlyzed for gadolinium concentration (μg/g) by ICP.

| Product of Example | Dose μg Gd/Kg | t½ min. | 7 Day Organ Retention | | |
|---|---|---|---|---|---|
| | | | Liver % | Spleen % | Kidney % |
| 19 | 831 | 98 | 9.9 | 1.3 | 0.7 |
| 19 | 1190 | 111 | 7.4 | 0.6 | 0.6 |
| 25 | 1764 | 69 | 24.0 | 11.8 | 0.5 |
| 26 | 1310 | 58 | 34.8 | 8.9 | 0.8 |

EXAMPLE 31

Biodistribution (2-Aminoethyl)-D03A was labelled with $^{153}$Gd. The chelate was coupled to 1:1 Egg PC/Egg Glutaryl liposomes (100 nm) as in Example 13. The radiolabelled liposomes were injected in the tail veins of mice. Three mice were used for each time point. Samples of blood, liver, spleen, kidney and skin were counted at 1 d, 3 d, and 7 d. The percent injected dose retained in each organ was calculated and is presented below. The elimination half-life for the liver was 3.2 d.

Organ retention (% injected dose)

| | 1 day | 3 day | 7 day |
|---|---|---|---|
| Blood | 0.60 | 0.54 | 0.51 |
| Liver | 18.22 | 9.91 | 4.88 |
| Spleen | 0.86 | 0.79 | 0.69 |
| Kidney | 1.03 | 0.74 | 0.64 |
| Skin | 1.68 | 1.19 | 0.80 |

We claim:

1. A biodegradable blood pool contrast agent having an overall molecular weight of at least 10 KD and comprising a non-liposomal molecular aggregate including a plurality of individual components, each individual component having formula (II):

C—D—E (II)

wherein C is a hydrophilic metal chelate-containing moiety, D is an opsonization-inhibiting moiety, and E is a hydrophobic moiety; the metal chelate-containing moiety being covalently bound to the opsonization-inhibiting moiety; and the individual components of the aggregate being held together by physicochemical effects.

2. A contrast agent as claimed in claim 1 wherein said opsonization-inhibiting moiety is an amphiphilic polymer moiety.

3. A contrast agent as claimed in claim 2 wherein said opsonization-inhibiting moiety is of formula (I)

—A—(R$_1$R$_2$)$_n$—B (I)

where A is a bond or a functional group allowing attachment to said macrostructure linked to (R$_1$R$_2$)$_n$ by a bond or a linker moiety, one of R$_1$ and R$_2$ is a lipophilic moiety, and the other of R$_1$ and R$_2$ is a hydrophilic moiety, n is an integer having a value of from 3 to 200, and B is a terminal group.

4. A contrast agent as claimed in claim 3 wherein repeat unit R$_1$R$_2$ is an alkyleneoxy, alkylenethio or alkyleneimino group.

5. A contrast agent as claimed in claim 1 wherein said opsonization-inhibiting moiety is a polyethyleneglycol moiety.

6. A contrast agent as claimed in claim 1 wherein said opsonization-inhibiting moiety is a glycosaminoglycan moiety.

7. A contrast agent as claimed in claim 6 wherein said opsonization-inhibiting moiety is a chrondroitin moiety.

8. A contrast agent as claimed in claim 1 wherein said opsonization-inhibiting moiety comprises 15 to 85% of the total weight.

9. A contrast agent as claimed in claim 1 wherein the individual components of said molecular aggregate have molecular weights of less than 15 KD.

10. A diagnostic composition comprising a contrast agent as claimed in claim 1 together with at least one physiologically tolerable carrier or excipient.

11. A process for the preparation of a contrast agent as claimed in claim 1, said process comprising metallating a macrostructure which has bound thereto a plurality of opsonization-inhibiting moieties and chelant groups.

12. A process for the preparation of a contrast agent as claimed in claim 1, said process comprising binding a plurality of opsonization-inhibiting moieties to a macrostructure which carries chelated ionic paramagnetic or heavy metal moieties.

13. A process for the preparation of a contrast agent as claimed in claim 1, said process comprising generating a macrostructure from a plurality of molecular components which plurality of components includes opsonization-inhibiting moieties and chelated ionic paramagnetic or heavy metal moieties.

14. A process for making a diagnostic composition comprising mixing a contrast agent as claimed in claim 1 together with at least one physiologically tolerable carrier or excipient.

15. A method of generating an image of a human or non-human animal body which method comprises administering into the systematic vasculature of said body an image enhancing amount of a contrast agent as claimed in claim 1 and thereafter generating an image of at least a part of said body.

* * * * *